US005565985A

United States Patent [19]
Fishkin et al.

[11] Patent Number: 5,565,985
[45] Date of Patent: Oct. 15, 1996

[54] PARTICLE MONITORING SENSOR

[75] Inventors: Boris Fishkin; Phil Salzman, both of San Jose, Calif.

[73] Assignee: Applied Materials, Inc., Santa Clara, Calif.

[21] Appl. No.: 486,169

[22] Filed: Jun. 6, 1995

Related U.S. Application Data

[63] Continuation of Ser. No. 88,975, Jul. 8, 1993.

[51] Int. Cl.$^6$ .................................................. G01N 21/03
[52] U.S. Cl. .......................................... 356/339; 356/246
[58] Field of Search ................................ 84/411 R, 413; 248/27.1; 356/336, 338, 339, 439, 244, 246; 250/222.2, 339

[56]             References Cited

U.S. PATENT DOCUMENTS

| | | | |
|---|---|---|---|
| 416,327 | 12/1889 | Durkee | 84/413 |
| 3,495,259 | 2/1970 | Rocholl et al. | 219/522 |
| 3,901,602 | 8/1975 | Gravatt, Jr. | 356/114 |
| 4,355,861 | 10/1982 | Sebald | 350/61 |
| 4,827,143 | 5/1989 | Munakata et al. | 356/339 |
| 5,083,865 | 1/1992 | Kinney et al. | 356/338 |

FOREIGN PATENT DOCUMENTS

| | | | |
|---|---|---|---|
| 210996 | 6/1994 | German Dem. Rep. | |
| 60-11146 | 1/1985 | Japan. | |
| 1354072 | 11/1987 | U.S.S.R. | 356/339 |

OTHER PUBLICATIONS

B. Fishkin, "In Situ Particle Monitoring Benefits in Tungsten Applications." *Ultraclean Manufacturing Conference 93*, p. 75.

L. Peters, "20 Good Reasons to Use In Situ Particle Monitors", *Semiconductor International*, pp. 52–57.

S. Gonzales, et al., "Particle Reduction Techniques and Performance Utilization on the AMAT Endura 5500 PVD System", *Microcontamination Conference Proceedings*, pp. 14–22.

D. Greenstin, et. al., "Investigating a Prototype in Situ Particle Monitor on the Exhaust Line of a CVD Reactor", *Microcontamination (Mar. 1991)*, pp. 21–26.

TSI Incorporated, "Vacuum Particle Detector Models 7320 and 7340", *TSI* (Product Information Brochure).

High Yield Technology, Inc., "Model 30 Sensor", (Product Information Brochure).

High Yield Technology, Inc., "Model 20S Sensor", (Product Data Sheet).

*Primary Examiner*—Richard A. Rosenberger
*Attorney, Agent, or Firm*—Raymond Kwong; Michael M. Gerardi; Rod S. Berman

[57]              ABSTRACT

An improved particle monitoring sensor is described which uses a variety of techniques to prolong the effective life of the optical surfaces within the particle monitoring sensor. Substantially inert purging gas is directed over the particle monitoring sensor windows, which are normally exposed to a harsh operating environment. The surfaces of these windows are heated by heating elements in direct thermal contact with the windows. In addition, a restrictive slit is placed over the detector window to reduce the exposed area and to increase the velocity of gas flowing over the window surface. While this slit reduces the detector's field of view, the signal loss is reduced by using a linearly polarized light source and aligning the elongated slit's major axis with the direction of polarization.

10 Claims, 3 Drawing Sheets

PARTICLE MONITORING SENSOR

This is a division of application Ser. No. 08/088,975, filed on Jul. 8, 1993.

BACKGROUND OF THE INVENTION

The diminished size of structures in modern semiconductor devices places extreme demands on semiconductor processing equipment. For example, the use of 0.35 µm design rules requires very low levels of particulate contamination throughout the processing environment. Recently, in situ particle monitors have been identified as potentially useful tools for monitoring the performance of semiconductor processing equipment. It is believed that, under certain circumstances, the output of in situ particle monitors can be correlated with the presence of undesirable levels of particulates in the reaction environment. Both developmental and production line semiconductor processing equipment may incorporate laser-based optical systems for monitoring particulate levels in exhaust gas flow as a measure of equipment cleanliness.

During processing, particulates created in the equipment chamber are withdrawn from the chamber and flow through the exhaust line of the chamber. Typically, particle monitors are laser-based optical systems designed to detect the low levels of scattered light produced when the laser light interacts with the particulate matter in the exhaust line flow. Sustained operation of such particle monitoring sensors is made difficult by the harsh chemical environment that exists in the exhaust line flow of semiconductor processing equipment. Chemical species within the exhaust gases deposit on the walls of the exhaust lines, and these species may deposit on or etch surfaces that are not suitably inert to the exhaust gas environment. Optical surfaces which face the interior of the exhaust line, such as those necessary for a low light level optical detection system, are quickly degraded in such an environment.

Increased scattering in the particle monitoring sensor's optical path may significantly diminish the signal to noise ratio for the sensor and thereby render it ineffective. For example, particulate matter deposited on the detector windows can reduce the level of light gathered by the collection optics, reducing the total signal level. In addition, a poor optical surface on the laser inlet window can scatter the input laser beam and the scattered beam may enter the detector, introducing an optical noise signal into the particle monitoring sensor. This noise signal can be so strong that no particle detection would be possible. As a consequence, the reactor must be taken out of service frequently to service the particle monitoring sensor by cleaning or replacing the optical surfaces. Because existing particle monitoring sensors are often integral parts of the reactor exhaust system, such servicing renders the host equipment inoperable and reduces the practicality of particle monitoring sensors.

One solution to the problem of degraded optical surfaces in exhaust line particle monitoring sensors is discussed in U.S. Pat. No. 5,083,865, entitled "Particle Monitoring System and Method." That patent describes a particle monitoring system which incorporates a number of strategies to limit the degradation of the optical surfaces in the described particle detector. One technique described is to direct a flow of clean gas across the optical surfaces of the particle detector. This gas flow impedes the diffusion of exhaust gases to the optical surfaces within the exhaust line. However, for particularly harsh environments, substantial flow rates across the optical surfaces are necessary to prevent damage to the optical surfaces. Such substantial flow rates are, in general, undesirable because the gas flowing into the exhaust line adversely affects the vacuum and flow characteristics of the reaction chamber.

Another technique described in the '865 patent limits the degradation of optical surfaces by heating the optical surfaces to suppress deposition from the exhaust gases onto the surfaces of the particle monitoring system optical surfaces. In the described system, a large heater is attached to the exhaust line upstream from the particle detection system. Heat is input to the exhaust line to heat the surfaces of the windows of that particle monitoring system. In practice, less heat than is input actually reaches the windows, probably because of the relatively low thermal conductivity of the stainless steel exhaust line. For high heating levels, an undesirable amount of heat may propagate through other parts of the particle monitoring system. This heat increases the operating temperature of both the semiconductor photodetector and the semiconductor laser diode, diminishing the performance and reducing the lifetime of both elements.

SUMMARY OF THE INVENTION

In accordance with one aspect of the present invention, a particle monitoring sensor comprises a chamber through which particulate matter flows. A coherent light source directs light into the chamber, where the light interacts with the particulate matter to produce a scattered light signal. A portion of the scattered light passes through a collection optical element to an optical detector. A heating element is disposed in thermal contact with the collection optical element but is in poor thermal contact with the optical detector. In this way, the heating element maintains the collection optical element at an elevated temperature.

In accordance with another aspect of the present invention, a particle monitoring sensor comprises a linearly polarized laser which emits light toward a scattering region. The particle monitoring sensor also includes a detector and collection optics, wherein the detector, the collection optics and at least a portion of the scattering region lie along an optical path. A slit is disposed along the optical path. The elongated axis of the slit is disposed substantially perpendicular to the polarization direction of the laser light.

In accordance with a further aspect of the present invention, a stream of substantially nonreactive gas is directed over at least some of the optical surfaces within a particle monitoring sensor.

BRIEF DESCRIPTION OF THE DRAWINGS

FIG. 4 is a schematic illustration of a slit assembly in accordance with an aspect of the present invention.

DETAILED DESCRIPTION OF THE INVENTION

The present invention is directed to a particle monitoring sensor. In preferred embodiments of the present invention, the optical surfaces of a particle monitoring sensor are protected from optical deterioration using one or more of the aspects of the present invention. Such optical surfaces might be the surfaces of windows which face on the processing environment within a piece of semiconductor processing equipment. One aspect of the present invention may utilize a field of view limiting slit to reduce the amount of optical surface area exposed to the processing environment. Preferably, this embodiment of the present invention is used in conjunction with a coherent polarized light source disposed so that the scattered optical signal quality is only slightly reduced from the levels observed without the field of view limiting slit.

Another aspect of the present invention incorporates a heater in thermal contact with one or more of the optical surfaces of the particle monitoring sensor. Preferably, the heater is in much better thermal contact with the optical surface than with either the light source or the detector of the particle monitoring sensor. In accordance with a different aspect of the present invention, a stream of substantially inert gas is directed across the optical surfaces of the particle monitoring sensor that face on the processing environment.

Preferred embodiments of the present invention are used in conjunction with semiconductor processing equipment such as the chemical vapor deposition reactor described in U.S. Pat. No. 4,872,947, which is entitled "CVD of Silicon Oxide Using TEOS Decomposition and In-Situ Planarization Process." Certain embodiments of the present invention may be used for process monitoring in semiconductor equipment. One such application is described in U.S. Pat. No. 5,083,865 entitled "Particle Monitor System and Method," owned by the assignee of the present invention, the disclosure of which is hereby incorporated by reference. However, it will be obvious from the following description that the teachings of the present invention may be applied to any particle monitoring sensor which operates at least partially in a harsh environment.

An embodiment of the present invention is illustrated in the accompanying figures. For convenience, the embodiment of the present invention illustrated in the figures will be described in conjunction with one of its preferred applications, that of a particle monitor situated along the exhaust line of a piece of semiconductor processing equipment. Other applications are, of course, possible.

Figure 1:
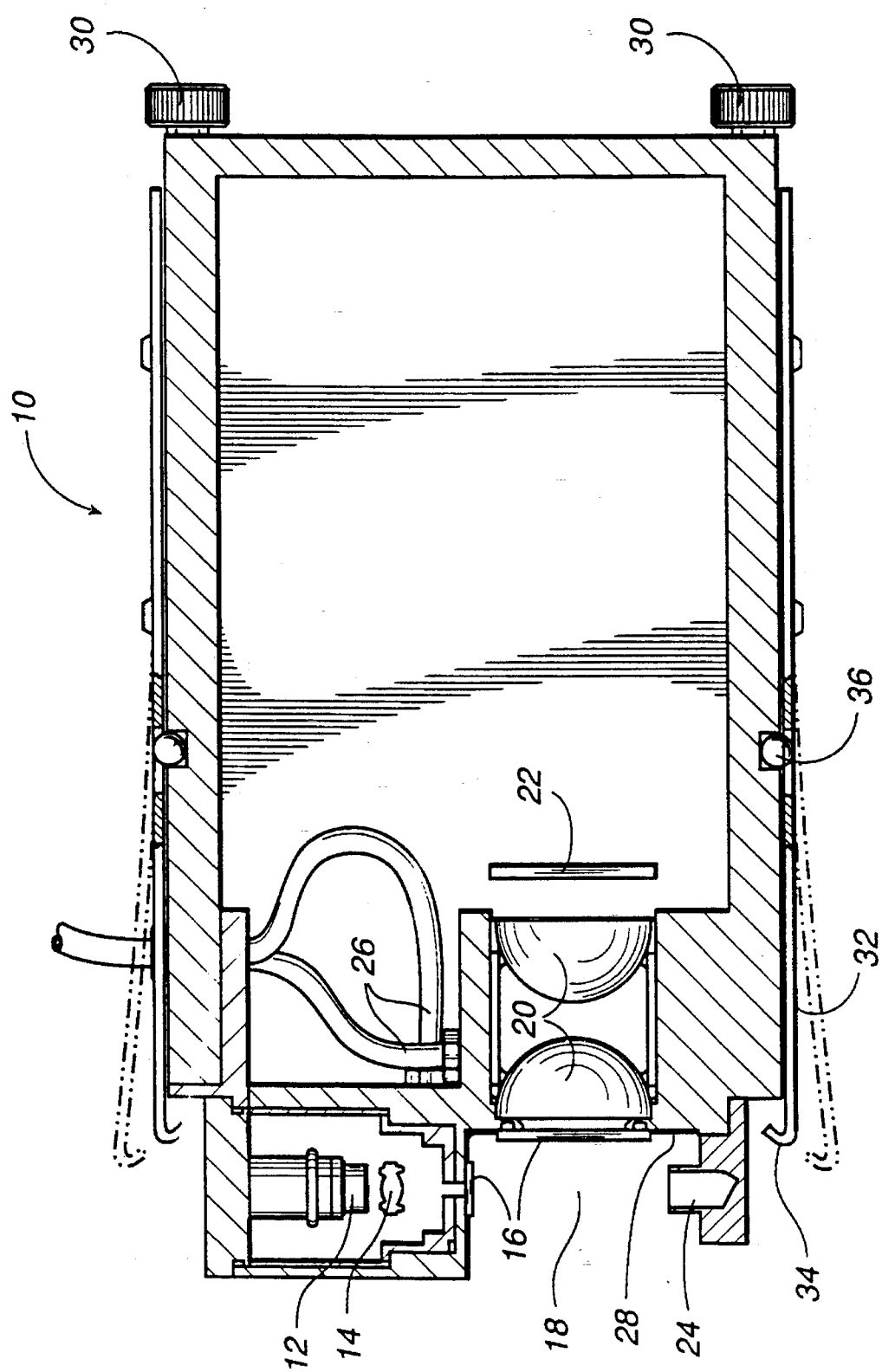
FIG. 1 shows a cross-sectional view of a particle monitoring sensor in accordance with the present invention.

FIG. 1 shows a particle monitoring sensor in cross section. The particle monitoring sensor, indicated generally at 10, includes one or more optical surfaces which face on the processing environment of the semiconductor processing equipment. For example, such optical surfaces may be present on the windows 16, through which light passes in the illustrated embodiment of a particle monitoring sensor. In preferred embodiments of the present invention, the light source optics 14 and collection optics 20 are separated from the harsh chemical environment within the exhaust line by windows 16. Ideally, the windows 16 should be hard, easily cleaned and highly transmissive at the wavelengths emitted by the light source. For example, quartz windows may be suitable in some applications, and magnesium fluoride or aluminum oxide may be suitable in others.

The present invention may utilize any of a number of techniques to limit the operational degradation of the optical surfaces of the windows 16. For example, in preferred embodiments of the present invention's particle monitoring sensor, a substantially non-reactive purge gas flows through gas lines to controlled flow connectors 26 and over the surface of the windows 16. Additionally, a thin film heater, indicated generally at 28, may be used to heat the surface of the windows 16. Finally, field of view limiting slits (not shown in FIG. 1) may be incorporated to reduce the portion of the windows 16 that are exposed to the harsh chemical environment of the exhaust line. By also using a polarized light source, the signal to noise ratio of preferred embodiments of the present invention is not unacceptably diminished by using a slit.

The particle monitoring sensor 10 includes a light source 12 which may be, for example, a 50 mW semiconductor laser operating at about 780 nm. Light output by light source 12 is collimated and shaped by optical elements 14. The optical elements 14 may include a cylindrical lens and an aspheric lens of the sort typically used for collimating the output beam of semiconductor diode lasers. After being collimated and shaped, the light from light source 12 passes through the wall of the exhaust line to form an input optical beam. The input optical beam enters the chamber defined by the wall of the exhaust line. While in this chamber, the input optical beam may be scattered by interacting with particulate matter or gases within the exhaust flow. The region of interaction is indicated generally at 18 in FIG. 1.

A portion of the scattered light will be scattered in the direction of the collection optics 20, which collects the incident scattered light and directs it to the detector 22. In preferred embodiments of the present invention, the collection optics 20 comprise a pair of aspheric lenses that image the scattering region onto the detector 22. To optimize the effective size of these lenses, each lens may be held in place by a number of small mounting fingers disposed at the edge of each lens. These mounting fingers can be arranged so that it is unlikely that any scattered light will be incident on the mounting fingers. Many different types of photodetectors are suitable for use with the present invention. For example, the commercially available photodiode S2551-01 manufactured by Hamamatsu may be used. As will be clear from the discussion below, the long and narrow geometry of the Hamamatsu S2551-01 is well suited for use with the scattering and detection arrangement illustrated in the figures. The output of the photodiode may be collected by any of the well known means for data collection and may be translated into a form that is compatible with standard data manipulation techniques.

The beam produced by the laser diode 12 is preferably shaped into an elongated beam with the breadth of the beam being substantially perpendicular to the flow direction of the gas. In addition, the junction of the laser diode will preferably be substantially aligned with the flow direction of the exhaust gases. Because the laser beam diverges most rapidly in the direction perpendicular to the diode junction, this alignment will also broaden the beam width in the scattering region. In this geometry, a greater proportion of the cross section of the exhaust line is illuminated. Accordingly, more scattering interactions between the input optical beam and the exhaust gas particulates should occur, and more of the particulate matter flowing in the exhaust line should be detected. Use of this increased scattering geometry is preferably accompanied by using a long, narrow detector. Such a detection geometry allows a greater cross sectional area of the exhaust line to be imaged onto the detector.

Much of the input optical beam that is not scattered in scattering region 18 passes through the chamber to the opposite surface of the wall of the exhaust line, where the optical beam preferably enters a light trap 24. A light trap is incorporated in preferred embodiments of the present invention, even for the 90° observation geometry shown in FIG. 1. This is because the use of a light trap reduces the amount of the input optical beam that is reflected within the chamber defined by the exhaust line wall. If the relatively intense input optical beam is allowed to reflect off of the exhaust line wall, the reflected light may create an unwanted background light signal that may be collected by the detector. A light trap will, in general, be useful for any collection geometry and, in particular, some form of light trap is desirable when the scattered light is being collected in the forward scattering direction.

The light trap shown at 24 may be formed, for example, from delrin. Delrin is acceptable because it is readily machinable and because its inner surface can be made to be relatively nonreflecting and relatively absorptive. The back surface of the light trap is preferably canted, that is, the back surface is formed at an angle so that it is not perpendicular to the propagation direction of The input optical beam. This canted back surface causes the light that is reflected from the back surface to be directed to the sidewalls of the light trap so that the light not initially absorbed undergoes a number of additional reflections.

Figure 2:
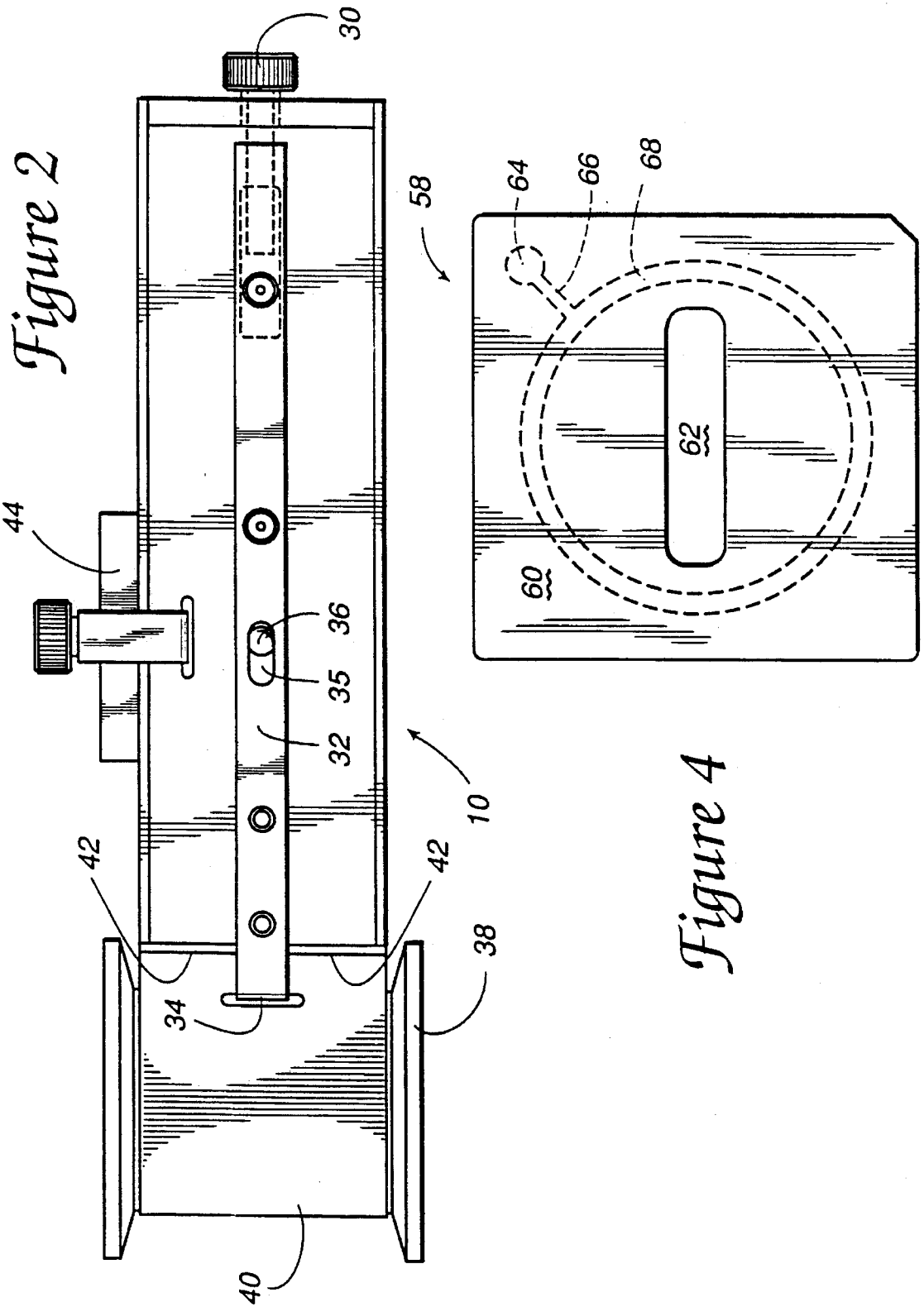
FIG. 2 shows a side view of a particle monitoring sensor of the present invention.

Referring now to FIG. 2, the particle monitoring sensor is shown in side view. In that figure, the particle monitoring sensor is coupled to a section of exhaust line, indicated generally at 40 in that figure. As is typical in the art, vacuum flanges 38 are provided for mounting the section of the exhaust line into the exhaust line vacuum system. In some of the embodiments of the present invention, KF flanges ranging from about one inch up to four or more inches in diameter may be used in the section of exhaust line 40. In this way, the particle monitoring sensor of the present invention can be readily adapted to a variety of operating environments. The illustrated section of exhaust line has been modified to include a substantially rectangular opening with a flat surface, indicated generally at 42. When the particle monitor is installed on the modified exhaust line, a flat surface on the particle monitoring sensor (shown at 50 in FIG. 3) is mated to the flat surface 42 surrounding the rectangular opening in the modified exhaust line 40. Preferably a seal of the O-ring type is used to obtain a vacuum junction between the exhaust line and particle monitoring sensor.

A particle monitoring sensor of the present invention is, in preferred embodiments, a compact unit that is field serviceable. In this sense, a field serviceable particle monitoring sensor should be removable without causing a prolonged shut down of the host processing reactor. It is desirable that the particle monitor be designed ergonomically for ease of removal and so that the same configuration of particle monitoring sensor can be used in a variety of operating environments.

One aspect of the field serviceability of the described particle monitoring sensor is a simplified mounting system. By turning knobs 30 in one direction, the particle monitoring sensor is securely attached to the modified exhaust line 40 and the O-ring is compressed to form a vacuum seal. By turning the knobs 30 in the opposite direction, and by removing detachable gas lines and electrical connections, the particle monitoring sensor can be removed from the exhaust line for servicing. Each of the knobs 30 is coupled to a strap 32 which is slidably mounted along the side of the illustrated particle monitoring sensor. Turning the knob 30 associated with strap 32 causes the strap 32 to slide toward the particle monitoring sensor and causes the hook 34 on the end of the strap to engage a slot on the side of the wall of the exhaust line 40. In preferred embodiments of the present invention, the strap 32 may be a durable metal such as stainless steel.

When the knobs 30 are turned in the opposite direction, the strap 32 slides away from the particle monitoring sensor, disengaging the hook 34 from the receptacles in the exhaust line 40. A preferred embodiment of the strap system incorporates a slot in the strap 32 which slides over the surface of nylon ball 36. When the strap 32 is withdrawn so that the hook 34 is near its engaging position, the slot 35 is disposed about the nylon ball 36 so that the strap is disposed near the side of the particle monitoring sensor. As the strap 32 is extended to disengage the hook 34, the slot 35 in the strap moves over the surface of the nylon ball until the slot 35 is no longer disposed about the nylon ball 36. The strap 32 then rides up and onto the surface of the nylon ball 36 and the strap moves away from the side of the particle monitoring sensor. Consequently, the hook 34 moves away from the wall of the exhaust line section 40. The particle monitoring sensor can then be readily withdrawn with little opportunity for the hooks 34 to engage the hook receptacles in the wall of the exhaust line section 40. While this hook disengaging feature of the present invention has been described in terms of a slot moving over a nylon ball, it is to be understood that other mechanisms could also be used. For example, materials other than nylon could be used so long as they are relatively durable and are well suited to a sliding arrangement. Other geometries could also be used. For example, a nylon wedge could be coupled with a depression in the strap to provide the same function.

It may also be desirable to use a plate to seal the opening in the exhaust line 40 when the particle monitoring sensor has been removed for servicing. Such a plate might conveniently be mounted on the particle monitoring sensor when it is not needed, such as is shown at 4, in FIG. 2.

Figure 3:
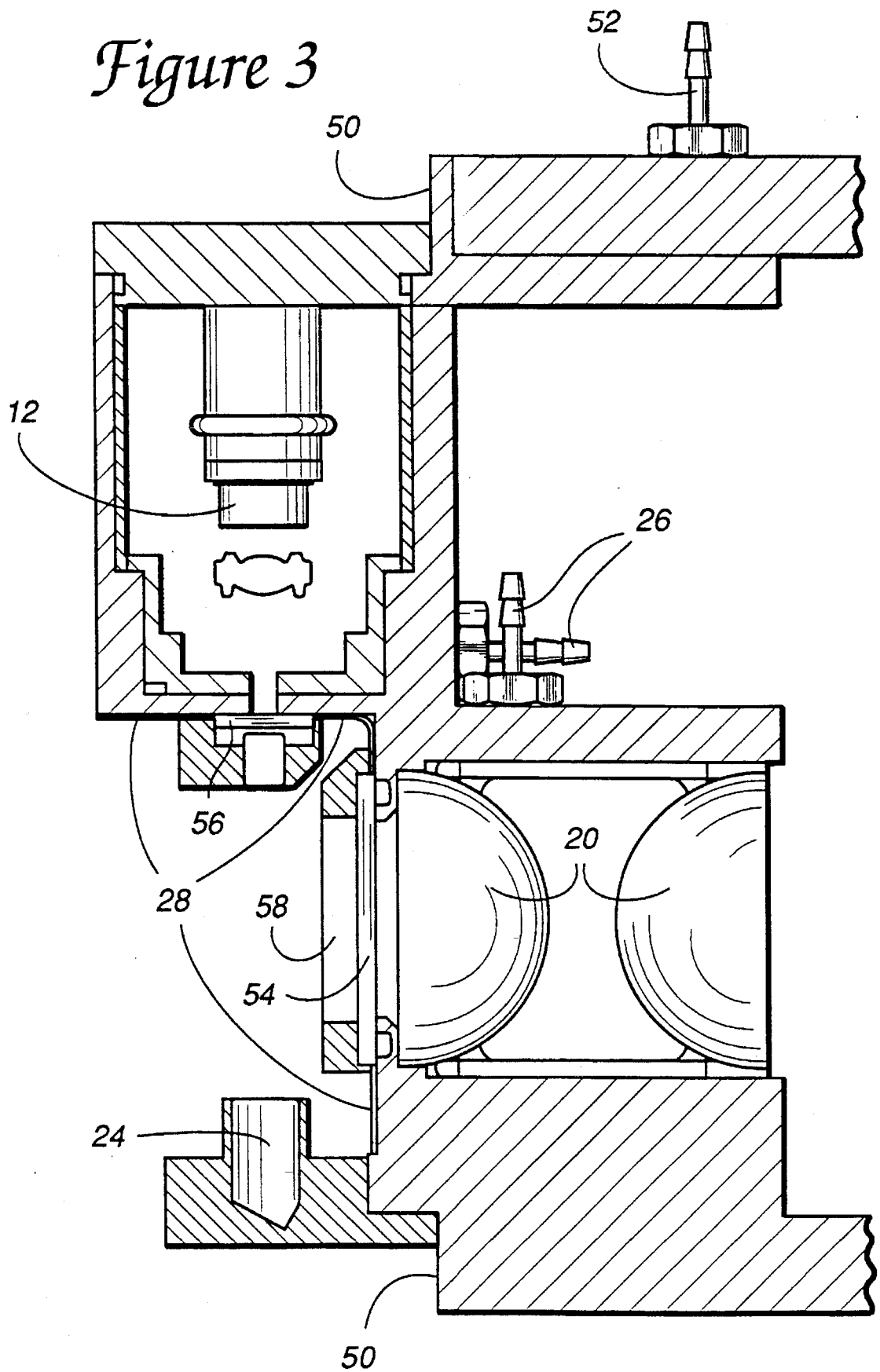
FIG. 3 shows an enlarged cross-sectional view of a portion of a particle monitoring sensor of the present invention.

Referring now to FIG. 3, a window purging system in accordance with one aspect of the present invention is described. Purge gas flows across the optical windows within the particle monitoring device, including the window 56 between the laser and the chamber and the window 54 between the detector and the chamber. Suitable gases for purging will be substantially inert and readily available in the semiconductor processing environment. For example, nitrogen gas ($N_2$) is used in the illustrated embodiment of a particle monitoring sensor.

Purge gas enters the particle monitoring sensor through, a detachable mechanical fitting coupled to the barbed inlet 52. The gas flows through fitting 52 and through connecting hoses (shown in FIG. 1, but not in FIG. 3) to one or more barbed inlets 26. Some of the purge gas flows over the laser, window 56 and some flows over the detector window 54. The barbs are filled with sintered metal plugs (a standard commercial product) to control the flow rates into each of the two gas channels formed in the structures on which the windows are mounted. In such plugs, the sintering conditions can be varied to produce plugs of increasing density which are correspondingly more restrictive to gas flow. In the illustrated embodiment, the flow rate to the smaller (laser) window is approximately 10 cc/min and the flow rate to the larger ($\approx$25 mm diameter) window is approximately 20 cc/min. The respective gas channels direct the purge gas to each of the windows. Ports at the end of the gas channels are arranged around the windows so that the purge gas flows radially inward across the windows. A plenum is preferably disposed at the periphery of the larger window to distribute the gas uniformly around the exterior of the window.

An example of a plenum for directing the purge gas flow over the surface of the window is shown in FIG. 4. In the illustrated embodiment, a slit assembly 58 is disposed in front of the detector window so that a plate 60, preferably of plastic, but which may also be of metal or other suitable material, partially encloses a space between the plate and the detector window. Light passes through a substantially rectangular slit 62 disposed in plate 60 before it passes through the detector window. Purge gas enters the space between the plate and the window through a slit port 64 (shown as a dashed line) and passes along a slit gas channel 66 which is connected to slit gas channel (plenum) 68. Gas flows through the channel defined by plenum 68 and then radially inward, flowing over the surface of the detector window. Of course, other plenums could be used which direct gas flows over the surface of a window without using a plastic or metal plate. In addition, the gas flow need not be radial and might be, for example, linear.

The velocity at which purge gas flows over the windows may be increased by placing a slit assembly, such as the one shown at 58 in FIGS. 3 and 4, in front of the surface of the windows. Gas flowing from behind the slit assembly would be forced through a slit 62, which would have the effect of throttling the gas flow, increasing the velocity of the flowing gas without increasing the total flow volume. For example, a slit assembly 58 may be placed in front of the detector window 54, increasing the flow velocity over the exposed surface of the window. Necessarily, the slit 58 reduces the field of view of, the detector 22, reducing the proportion of the scattered light that is collected. Accordingly, there will be an empirical trade off between the flow velocity over the window and the field of view of the detector. As is discussed below, when polarized light is used in the present invention, and when certain scattering geometries are used, the signal lost by reducing the slit size may be relatively small in comparison to the greater flow velocity that can be achieved in accordance with the present invention.

The quality of the purge—that is, the amount of purge gas that flows by the windows—is limited by the vacuum environment of the reactor. It is preferable to have a large volume of gas flowing over the optical surfaces exposed to the exhaust line environment. A large gas flow limits the proportion of chemically reactive species that will diffuse to the optical surfaces of the particle monitoring sensor. However, too much purging gas flow into the exhaust line will impair the operation of the reactor. The smaller slit allows the total purging flow rate to be reduced, while maintaining a sufficient flow so as to limit damage to the windows.

The particle monitoring sensor described in U.S. Pat. No. 5,083,865 heats the optical surfaces of the particle monitoring sensor by heating the exhaust line above the particle monitoring sensor. This design has certain drawbacks when used to substantially heat the optical surfaces. First, the heat transfer is inefficient. This is because there are, a number of interfaces for the heat to cross to reach the windows. Additionally, the primary pathway for thermal conductance is along the stainless steel exhaust line. Stainless steel is one of the poorest thermal conductors of the metals. Thus, it would be preferable to improve the thermal contact between the heater and the optical surfaces of the particle monitoring sensor.

When it is desired to heat the optical surfaces of the particle monitoring sensor to a substantial extent, the poor heat transfer of stainless steel may lead to the injection of extraneous heat into the particle monitoring sensor. This excess injection of heat is undesirable because both the detector and the laser diode are sensitive to heat. In particular, failure rates for laser diodes increase significantly for temperatures even moderately elevated above room temperature. Operating currents also increase significantly for increased temperatures, causing the laser diode to dissipate even larger amounts of heat, creating a thermal runaway condition. Thus, it is undesirable to apply excessive amounts of heat to the particle monitoring sensor.

In accordance with a preferred embodiment of the present invention, heat is applied locally to the windows of the particle monitoring sensor. This allows the windows to be more effectively heated without affecting either the detector or the laser diode. In the illustrated particle monitoring sensor, a flexible resistive heater 28 is clamped in close proximity to both the window 56 associated with the laser diode and the window 54 associated with the detector. A generally circular heating element is disposed at the periphery of each of the windows so that the heater comprises two distinct heating elements. The two heating elements are connected in series and may be driven with a single power source. The glass of each of these windows presses the heater against an O-ring and a spacer so that the heater is in close physical and thermal contact with the window. The heater 28 itself is a thin, resistive film of metal sandwiched between two insulating Kapton films, so that the entire heater is about 0.007" thick and is-easily flexible. Such heaters are well known in the art and are commercially available. For example, in one embodiment of the present invention, a 24 Ohm, 3.34 Watt, two-element heater is driven at 9 Volts to heat both of the windows in the particle monitoring sensor. Insulating materials with good high temperature stability other than Kapton could, of course, be used in the described heaters. The heater need not be flexible, though it is preferred that the heater closely conform to the heated surfaces.

Using a heater of this design, it should be possible to heat the windows to temperatures approaching or even above 100° C., without substantially harming either the detector or the laser diode. Such temperatures are believed to, be desirable for protecting the particle monitoring sensor's windows during, for example, tungsten etch processes.

Heating of the laser diode 12 is minimized because the diode is thermally isolated from the laser window 56 by a plastic fitting and by a stainless steel or plastic housing. In addition, the diode is heat-sinked to an aluminum block, so the amount of heat flowing to the diode is relatively small. The detector 22 is similarly thermally isolated from the windows in the wall of the chamber.

in an alternate embodiment of the present invention, the heater 28 is not a separate element but instead comprises a thin metal film directly deposited on the surface of the window. The resistive metal film would be disposed away from the center of the window so that the heater does not block light. In still another embodiment, the thin film coating for use as a resistive heater is 80% to 90% transparent, and is applied over the open aperture of the window, or over the entire window including the open aperture. Such coatings are readily commercially available. Contacts are made in any of the well known fashions and the heater is driven in the same manner as is the heater discussed above.

In preferred embodiments of the present invention, light incident on particulate matter within the exhaust gas flow is partially absorbed and reradiated by the particulate matter within the exhaust gas flow. In reradiating the incident light, the particulate matter appears to absorb and radiate light in a fashion similar to that of a dipole oscillator. The optical radiation characteristics of a dipole oscillator are described in Hecht & Zajac, Optics 52–57, 242–45 (1979), which discussion is incorporated herein by reference. When linearly polarized light is incident on the particulate matter, most of the light will be scattered into the plane that is substantially perpendicular to the polarization vector of the light. Consequently, little light will be scattered into the directions that are substantially parallel to the polarization direction of the light. Most of the optical power produced by scattering interactions between the linearly polarized input light beam and the particulate matter will be emitted along the plane that is substantially perpendicular to the polarization direction of the incident light. Thus, the scattered optical power is expected to be distributed about the plane normal to the polarization direction, with the maximum of the optical power distribution lying substantially in that plane.

In preferred embodiments of the present invention, a linearly polarized semiconductor diode laser is used as an input light source for the particle monitoring sensor. In a particularly preferred embodiment of the present invention, the polarization vector of the light produced by the laser is aligned so that it is substantially aligned parallel to the direction of particulate flow in the exhaust line of the reactor. Thus, light incident on the particulate matter is expected to be scattered primarily into a plane lying substantially perpendicular to the direction of the polarization of the light produced by the laser. In addition, the linear path of the light produced by the laser preferably lies in substantially in that same plane.

In accordance with a further aspect of the present invention, it is preferred to place a slit in the path of the collection optics 20. This slit is preferably elongated and may be, for example, a slightly rounded, rectangular opening. The direction of elongation is disposed so that the elongation axis is substantially perpendicular to the direction of the polarization of the light input to the particle monitoring sensor. In the illustrated embodiment of the present invention, the slit is preferably elongated to correspond to the elongated detector 22 used in preferred embodiments of the present invention. The exact size of the opening will depend on where the slit is placed in the optical path and on the particular geometry of the particle monitoring sensor.

The preferred shape and dimension of the slit is preferably determined empirically by varying the slit size and geometry to optimize the detection area in an operating particle monitoring sensor. Other detection characteristics might also be used to optimize the slit. For example, the particle size detection limit or the total scattered signal might be maximized in evaluating different slits.

Preferred embodiments of the present invention use an opaque plate, such as slit assembly 58, disposed on the outside of the window 54. For example, a stainless steel or a plastic plate 60 with a rounded rectangular opening 62 may be placed to the exhaust line side of a round window in the wall of the exhaust line. Suitable plastic materials for this slit might be polyetheretherketone or the "VESPEL" material produced by the Dupont Corporation. This slit covers the round window with the exception of the rectangular opening in the slit. When this controlled slit aspect of the present invention is combined with the use of a purging gas flow over the optical surfaces of the particle monitoring sensor, the effect of the slit size on the volume of purge gas necessary to obtain the benefit of purging gas flow must also be considered in optimizing the slit shape and geometry.

In certain embodiments of the present invention, the collection window 54 and collection optics 20 may be sectioned so that the portions of the optics not normally involved in refracting scattered light are removed. This allows the total detector assembly to be made thinner.

Preferably, the present invention utilizes a 90° scattering geometry as illustrated in the figures. In other words, the collection optics are disposed so that their principal optical axis is disposed substantially perpendicular to the propagation direction of the incident light. The component of light scattered into the 90° direction is much smaller than the component scattered into the forward direction for particles that are relatively large compared to the wavelength of the illuminating light. However, because of other considerations discussed herein, improved-signal-to-noise ratios have been observed in accordance with the present invention when employing a 90° collection geometry.

In preferred embodiments of the present invention, the scattered light intensity diminishes as the collection angle deviates from the normal to the polarization plane of the incident light. Thus, the elongated slit used in accordance with certain aspects of the present invention will eliminate some scattering signal, but not an unacceptable amount. The smaller slit (4 mm×≈17 mm) reduces the detection cross section by only about 20% compared to the circular (≈17 mm diameter) aperture. That is, when observing the flow of 0.5 μm particles, the count rate for the elongated slit is about 80% of that observed for the circular aperture. This reduction is relatively small when considering the reduction in collection surface area when only a 4 mm×17 mm slit remains open from a window that is approximately 25 mm in diameter. Because there is little drop off in detection area, the smaller slit is preferred because of its ability to greatly improve the flow velocity over the window 54, thereby slowing the optical degradation of the collection optics window.

The present invention may also be practiced in a forward scattering geometry. When the light is collected in the forward direction, the main (unscattered) beam must be eliminated from the forward signal. In all cases, it is preferable for the scattered light signal to be measured in the dark field. The small slit arrangement described herein may also be used in the forward scattering collection geometry.

Additionally, by providing a smaller slit before the collection window, a smaller surface area of the collection window will be heated in preferred embodiments of the present invention. Accordingly, less power would need to be input to heat the surface of the window to the same or higher temperature.

While the present invention has been described with reference to specific preferred embodiments thereof, it will be understood by those skilled in this art that various changes may be made without departing from the true spirit and scope of the, invention. In addition, many modifications may be made to adapt the invention to a given situation without departing from its essential teachings.

What is claimed is:

1. A particle monitoring sensor comprising:

a chamber through which particulate matter flows, said chamber comprising a chamber wall including a plurality of hook receptacles;

a coherent light source producing an input optical beam;

an input window, said input optical beam passing through said input window into said chamber, said input optical beam interacting with said particulate matter within said chamber to produce an output optical signal;

a detector window, wherein at least a portion of said output optical signal passes through said detector window;

a detector, wherein at least a portion of said output optical signal which passes through said detector window is incident on said detector;

a substantially rectangular frame, said frame having two substantially parallel surfaces, wherein said input window and said detector window are disposed in a fixed relationship with said frame; and two straps slidably mounted to said parallel surfaces of said frame, each of said straps comprising a hook on one end of the strap such that when both of said hooks are engaged with said hook receptacles disposed on said chamber wall, said chamber is securely attached to said frame.

2. The particle monitoring sensor of claim 1 further comprising an O-ring compressed between said chamber wall and said frame.

3. The particle monitoring sensor of claim 1 wherein said frame comprises a ball and wherein at least one of said straps comprises a slot disposed about said ball.

4. The particle monitoring sensor of claim 1 wherein each of said straps is coupled to a knob and wherein each of said strap slides in response to said knob being turned.

5. The particle monitoring sensor of claim 1 such that when said hooks are disengaged, a portion of each of said straps is disposed away from said frame.

6. A method of disconnecting a particle detector comprising a plurality of knobs, a corresponding plurality of movable straps each of which is actuated by a different one of said knobs, and a plurality of surfaces, each said strap being adjacent to a surface of said particle detector, each said strap having a hook, from a section of an exhaust line of a semiconductor processing apparatus, said exhaust line section having defined therein a plurality of hook receptacles corresponding to said plurality of hooks, said method comprising the step of rotating said plurality of knobs whereby said plurality of straps retracts along said plurality of surfaces and thereby causes said plurality of hooks to disengage from said plurality of hook receptacles.

7. The method of claim 6 wherein said retraction of straps is effected together with a lateral displacement of said plurality of hooks away from said plurality of hook receptacles.

8. The method of claim 7 wherein a slot is defined in each of said plurality of straps, said plurality of surfaces each comprise a ball aligned with one of said slots, and said retraction of said straps causes said slots to retract with respect to said balls and subsequently causes said straps to contact said balls, resulting in said lateral displacement of said hooks.

9. The method of claim 7 wherein a depression is defined in each of said plurality of straps, said plurality of surfaces each comprise a wedge coupled with one of said slots, and said retraction of said straps causes said depressions to retract with respect to said wedges, resulting in said lateral displacement of said hooks.

10. The method of claim 6 wherein an O-ring is compressed between said particle detector and said section of said exhaust line to form a vacuum seal, and wherein said retraction of said straps releases compression on said O-ring.

\* \* \* \* \*